United States Patent [19]

Shukla et al.

[11] 4,201,677
[45] May 6, 1980

[54] INTUMESCENT COMPOSITION COMPRISING CYCLIC NITROGEN COMPOUND AND PHOSPHORUS COMPOUNDS

[75] Inventors: Jayendra G. Shukla; Ray E. Smith; Richard R. Nicholson, all of Ann Arbor, Mich.

[73] Assignee: Velsicol Chemical Corporation, Chicago, Ill.

[21] Appl. No.: 939,625

[22] Filed: Sep. 5, 1978

[51] Int. Cl.$^2$ .............................................. C09K 3/28
[52] U.S. Cl. .................................. 252/8.1; 427/325; 428/541; 428/921
[58] Field of Search ................. 252/8.1; 427/325, 421, 427/429, 440; 428/479.6, 541, 921

[56] References Cited

U.S. PATENT DOCUMENTS

| | | | |
|---|---|---|---|
| 3,906,136 | 9/1975 | Weil | 252/8.1 X |
| 4,085,283 | 4/1978 | Otter et al. | 252/8.1 X |

Primary Examiner—Leland A. Sebastian
Attorney, Agent, or Firm—Dietmar Olesch

[57] ABSTRACT

An intumescent composition comprising a cyclic nitrogen compound, an acid selected from the group consisting of phosphorous acid, phosphoric acid, and mixtures thereof, water, and an hydroxy-containing organophosphorus compound, wherein:

(a) said cyclic nitrogen compound is

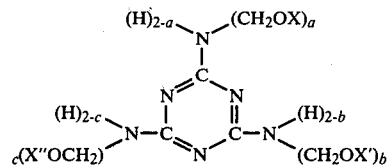

wherein a, b, and c are integers selected from the group consisting of 1 and 2, a plus b plus c equal about 3 to 6, and X, X', and X" are independently selected from the group consisting of hydrogen and —$CH_3$;

(b) said hydroxy-containing organo-phosphorus compound is selected from the group consisting of

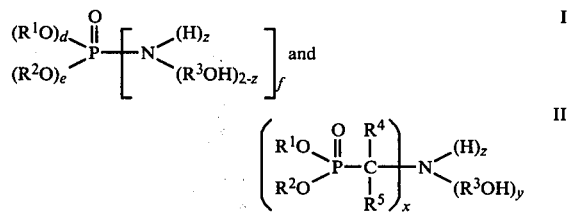

and mixtures thereof, wherein d is an integer of from 0 to 2, e is an integer of from 0 to 2, f is an integer of from 1 to 3, and d plus e plus f equal 3; z is an integer of 0 to 1; x is an integer of 1 to 2, y is an integer of 1 to 2, and x plus y plus z equal 3; $R^1$, $R^2$, and $R^3$ are selected from the group consisting of alkyl radicals containing from about 1 to about 6 carbon atoms and haloalkyl radicals containing from about 2 to about 6 carbon atoms, provided that when $R^3$ is haloalkyl it contains at least 3 carbon atoms; $R^4$ and $R^5$ are selected from the group consisting of hydrogen, alkyl radicals, and haloalkyl radicals, wherein said radicals contain from about 1 to about 6 carbon atoms; and the total number of carbon atoms in the $R^1$, $R^2$, $R^3$, $R^4$, and $R^5$ groups does not exceed about 14.

10 Claims, No Drawings

INTUMESCENT COMPOSITION COMPRISING CYCLIC NITROGEN COMPOUND AND PHOSPHORUS COMPOUNDS

BRIEF SUMMARY OF THE INVENTION

An intumescent composition containing a cyclic nitrogen compound, a phosphorus compound, phosphorous acid or phosphoric acid, and water is disclosed.

DETAILED DESCRIPTION

It is difficult to impart durable flame retardance to a wood substrate. Wood substrates present a flameproofing problem which is materially different from that presented by fibrous hydrophilic organic substrates. According to U.S. Pat. No. 2,927,050, in the latter substrate "... substantially independent fibers are tangled together, leaving interstices capable of being filled by an aqueous medium by capillary action between all of their surfaces. The individual fibers contain a relatively small amount of cellulose, and the materials composed of them have a relatively low ignition temperature." In wood substrates, however, "... the cellulosic fibers are bonded together to form a relatively impenetrable block susceptible to little capillary action. A piece of wood has small surface area in relation to the amount of surface area it contains and has a relatively high ignition temperature." Because of these factors, "... a flameproofing agent which flameproofs fibrous hydrophilic organic materials is not likely to flameproof wood because its capacity to inhibit burning is likely to be destroyed by the time it is heated to the ignition temperature of the wood and/or because of the difficulty of causing a non-volatile substance to penetrate into the volume of a block of wood."

Impregnation of a wood substrate with a fire-retardant is known in the art. U.S. Pat. No. 3,398,019 teaches that this method must be used to impart a satisfactory degree of flame retardancy to wood fiber insulation, stating that "as far as is known only by the use of a chemical retardant which impregnates the board can a commercially acceptable building material be produced which is capable of securing a nonflammable rating." U.S. Pat. No. 4,049,849 teaches that this method, although well known, presents several substantial problems. According to this patent, the use of a wood substrate impregnated with a fire-retardant salt is restricted to low humidity applications "... due to the water solubility and hygroscopicity of most known fire retardant salts." Thus, "... if an ammonium phosphate-impregnated wood substrate is exposed to high (greater than 90 percent) humidity at ambient temperature, in approximately 3 days the fire retardant impregnant (salt) will leach therefrom. "... The salt will absorb sufficient water vapor to enable it to migrate to the wood substrate surface. Not only does this leaching deplete the salt content of the wood substrate, rendering it less fire resistant, but it also severely disfigures the wood substrate's surface...."

Those in the art have attempted to impart durable flame retardance to wood substrates by applying intumescent compositions to them. Many intumescent compositions have been tested; U.S. Pat. No. 3,668,121 correctly states that only a few of them are of any value. Many of them produce excessive smoke and/or toxic gaseous pyrolysis products. According to U.S. Pat. No. 3,769,074, most of these prior art intumescent compositions are "... characterized by the disadvantages of high cost, low spreading rate, relatively poor efficiency, and poor weatherability." U.S. Pat. No. 3,513,114 teaches that prior art intumescent coating compositions" ... exhibit the distinct disadvantage of either or both failing to maintain a coating film which will withstand repeated scrubbing or washing and thus exhibit wet abrasion resistant properties and/or failing to perform their intended function, that is, to intumesce, and thus fire retard after repeated scrubbing or washing." U.S. Pat. No. 3,535,130 teaches that "... conventional intumescent paints are usually sensitive to attack by water. ..." U.S. Pat. No. 3,654,190 discloses that prior art intumescent compositions are water permeable and tend to degrade when exposed to moist environments.

U.S. Pat. No. 3,513,114 discloses that the problems presented by the prior art intumescent compositions cannot be solved merely by replacing the water soluble flame retardant agents they contain with water insoluble additives, for such substitution does not necessarily increase the wet abrasion resistance properties of the compositions. Furthermore, such a substitution will present a new set of problems if the water insoluble additive must be dissolved in an organic solvent; for many dangers are created by the use of the common organic solvents. Toluene, for example, is a fire hazard and an explosion hazard when exposed to heat and flame; and it emits toxic fumes. Methylene chloride is very dangerous to the eyes. Benzene is highly flammable, causes leukemia, and it is a known carcinogen. Acetone is a fire hazard when exposed to either heat or flame. Methanol possesses narcotic properties and exerts a toxic effect upon the nervous system; once it is absorbed into the body, it is eliminated very slowly and, thus, is a cumulative poison. The use of almost any of the common organic solvents will present some hazard.

Other prior art considered by applicants during the preparation of this application include U.S. Pat. No. 3,445,547 (preparation of bis [bis(hydroxymethyl)-butyl]hydrogen phosphate), U.S. Pat. No. 2,676,162 (an intumescent coating for wood containing organic solvent, methylated methylol melamine, the reaction product of ammonia and phosphoryl chloride, and a film-forming condensation product), U.S. Pat. No. 3,449,161 (fire-retardancy can be incorporated into paint compositions using organo-phosphorus amides), U.S. Pat. No. 3,635,970 (melamine phosphate is especially useful in intumescent paint compositions), U.S. Pat. No. 4,026,810 (an intumescent flame retardant prepared by reacting, e.g., phosphoric oxide, phosphoric acid, pentaerythritol, and melamine and thereafter curing the reaction product by heating to evolve gaseous products), U.S. Pat. No. 2,582,961 (an aqueous flame retardant for cellulosic fiber containing, e.g., methylated methylol melamine, methylol dicyandiamide, and an oxygen-containing acid of phosphorus), U.S. Pat. No. 2,661,342 (flameproofing of cellulosic materials with a resinous aminoplast condensation product such as melamine and a water-soluble nitrogen- and phosphorus-containing product), U.S. Pat. No. 3,023,176 (a water-soluble hardenable condensation product which is prepared by reacting a methylol compound of the aminotriazine group, an aliphatic compound containing a chain of at least 7 carbon atoms and a reactive hydrogen bound to a hetero atom, and a compound that is capable of introducing atomic groupings that raise the hydrophility in a non-ionic manner), U.S. Pat. No. 3,101,278 (methylolphosphorus polymers which have nitrogen atoms incorporated into them are excellent flame retardants and are suitable for treating cellulosic materials), and U.S. Pat. No. 3,332,240 (an aqueous solution for flameproofing cotton fiber containing a salt of hydroxylamine and melamine resin).

It does not appear that the prior art describes an aqueous composition which can impart durable flame retardance to wood substrates even after repeated exposure to water, which will form a coating film which withstands repeated scrubbing or washing, and which substantially decreases the amount of noxious fumes generated during pyrolysis of the treated wood substrate.

Applicants have discovered a unique intumescent composition which is superior to the intumescent coatings of the prior art.

In accordance with this invention, there is provided an intumescent composition comprising a cyclic nitrogen compound, phosphorous acid or phosphoric acid, water, and a phosphorus compound selected from the group consisting of

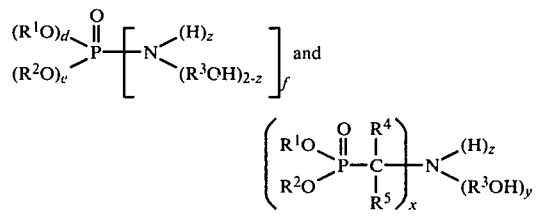

and mixtures thereof, wherein d is an integer of from 0 to 2, e is an integer of from 0 to 2, f is an integer of from 1 to 3, and d plus e plus f equal 3; z is an integer of 0 to 1; x is an integer of 1 to 2, y is an integer of 1 to 2, and x plus y plus z equal 3; $R^1$, $R^2$, and $R^3$ are selected from the group consisting of alkyl radicals containing from about 1 to about 6 carbon atoms and haloalkyl radicals containing from about 2 to about 6 carbon atoms, provided that when $R^3$ is haloalkyl it contains at least 3 carbon atoms; $R^4$ and $R^5$ are selected from the group consisting of hydrogen, alkyl radicals, and haloalkyl radicals, wherein said radicals contain from about 1 to about 6 carbon atoms; and the total number of carbon atoms in the $R^1$, $R^2$, $R^3$, $R^4$, and $R^5$ groups does not exceed about 14.

The intumescent coating composition of this invention contains a cyclic nitrogen compound of the formula

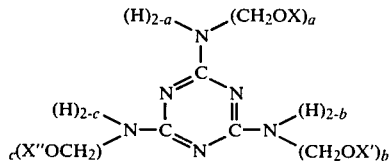

wherein a, b, and c are integers selected from the group consisting of 1 and 2, a plus b pluc c equal from about 3 to about 6, and X, X', and X" are independently selected from the group consisting of hydrogen and —$CH_3$. It is preferred that at least one of said X, X', and X" groups be —$CH_3$. It is more preferred that at least two of said X, X', and X" groups be —$CH_3$. It is most preferred that each of said X, X', and X" groups be —$CH_3$.

It is preferred that the intumescent composition of this invention contain from about 30 to about 60 percent (by weight) of said cyclic nitrogen compound; in a more preferred embodiment, the composition of this invention contains from about 35 to about 50 percent (by weight) of said cyclic nitrogen compound. As used in this specification, the term "percent" refers to the weight percent of the component referred to; it is calculated by dividing the weight of the component by the combined weight of all the components and multiplying the ratio so obtained by 100.

The cyclic nitrogen compound used in the composition of this invention may be prepared by reacting formaldehyde with melamine and then etherifying the methylol groups by reaction of the methylol melamine with methanol in the presence of an acid catalyst. This melamine product is a water-soluble material in the incompletely condensed state.

The intumescent composition of this invention contains a phosphorus compound selected from the group consisting of

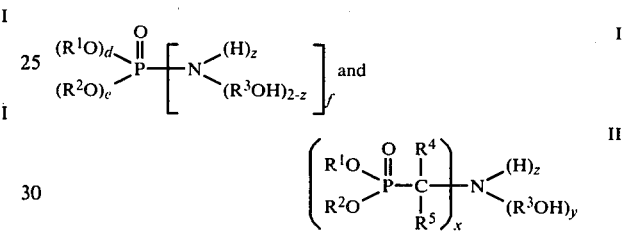

and mixtures thereof, wherein d is an integer of from 0 to 2, e is an integer of from 0 to 2, f is an integer of from 1 to 3, and d plus e plus f equal 3; z is an integer of 0 to 1; x is an integer of 1 to 2, y is an integer of 1 to 2, and x plus y plus z equal 3; $R^1$, $R^2$, and $R^3$ are selected from the group consisting of alkyl radicals containing from about 1 to about 6 carbon atoms and haloalkyl radicals containing from about 2 to about 6 carbon atoms, provided that when $R^3$ is haloalkyl it contains at least 3 carbon atoms; $R^4$ and $R^5$ are selected from the group consisting of hydrogen, alkyl radicals, and haloalkyl radicals, wherein said radicals contain from about 1 to about 6 carbon atoms; and the total number of carbon atoms in the $R^1$, $R^2$, $R^3$, $R^4$, and $R^5$ groups does not exceed about 14.

It is preferred that the intumescent composition of this invention contain from about 10 to about 55 percent (by weight) of said phosphorus compound. In a more preferred embodiment, said composition contains from about 20 to about 50 percent (by weight) of the phosphorus compound.

In a preferred embodiment, the phosphorus compound is soluble in either the water and/or the acid components of the composition; in this preferred embodiment, when one part of the phosphorus compound is mixed with no more than one part of the component in which it is soluble at 25 degrees centigrade, a one-phase solution is obtained.

The phosphorus compound described by formula I may be made by methods well known to the art. Thus, for example, some of these may be prepared in accordance with the following reaction scheme:

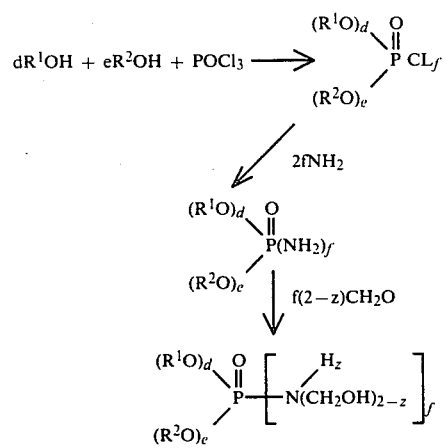

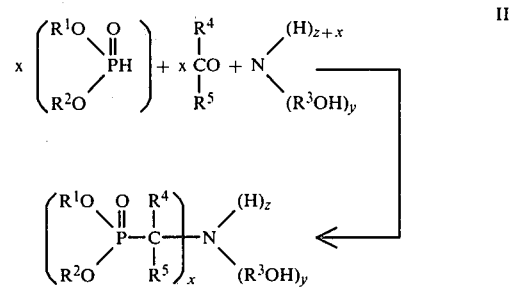

Some of the preferred phosphorus compounds which are described by formula I and can be utilized in the intumescent composition of this invention are, e.g., diethyl-N,N-dimethylol phosphoramidate, trichloroneopentyl-chloroethyl-N,N-dimethylol phosphoramidate, dimethyl-N,N-dimethylol phosphoramidate, methyl ethyl-N,N-dimethylol phosphoramidate, hexyl ethyl-N,N-dimethylol phosphoramidate, tribromoneopentyl methyl-N,N-methylol phosphoramidate, propylpentyl-methylol phosphoramidate, diethyl-N-methylol phosphoramidate, methylpropyl-N,N-dimethylol phosphoramidate, ethyl propyl-N-methylol phosphoramidate, dibutyl-N,N-dimethylol phosphoradmiate, pentyl butyl-N,N-dimethylol phoshoradmidate, dipropyl-N,N-dimethylol phosphoramidate, bis-2-bromomethyl-N,N-dimethylol phosphoramidate, chloroethyl-chloroneopentyl-N,N-dimethylol phosphoramidate, bis-(2-chloroethyl)-N,N-dimethylol phosphoramidate, bis-(2,3-dibromopropyl)N,N-dimethylol phosphoramidate, and the like. Mixtures of these compounds also may be utilized.

Other phosphorus compounds described by formula I which can be utilized in the intumescent composition of this invention include, e.g., hexamethylol phosphorotriamidate, chloroneopentyl-N,N,N'N'-tetramethylol phosphorodiamidate, chloroethyl-N,N'-dimethylol phosphorodiamidate, and the like. Mixtures of these compounds may be utilized.

The phosphorus compound described by formula II may be prepared by conventional methods well known to the art. Thus, the following reaction scheme may be used:

When a compound described by formula I or formula II is used as a phosphorus source in the intumescent composition of this invention, it is preferred that z be zero, that $R^1$ and $R^2$ be independently selected from the group consisting of alkyl radicals containing from about 1 to about 4 carbon atoms and haloalkyl radicals containing from about 2 to about 4 carbon atoms, that $R^3$ be alkyl of from about 1 to about 4 carbon atoms, and that $R^4$ and $R^5$ be hydrogen. In a more preferred embodiment, x is 1 and $R^1$ and $R^2$ are independently selected from the group consisting of ethyl and haloethyl.

When $R^1$ and $R^2$ are haloalkyl, the halogen substituent(s) is selected from the group consisting of bromine, chlorine, or mixtures thereof.

Some of the phosphorus compounds which are described by formula II and which can be utilized in the intumescent composition of this invention include, e.g., the phosphorus compounds described in Table I. Mixtures of these compounds also may be utilized. Other comparable compounds will readily suggest themselves to those skilled in the art for use in the intumescent composition of this invention; they are also intended to be comprehended within the scope of this invention.

TABLE I

| $R_1$ | $R_2$ | $R_3$ | $R_4$ | $R_5$ | X | Y | Z |
|---|---|---|---|---|---|---|---|
| ethyl | ethyl | ethylene | H | H | 1 | 2 | 0 |
| chloroethyl | chloroethyl | ethylene | H | H | 1 | 2 | 0 |
| methyl | methyl | propylene | H | H | 1 | 2 | 0 |
| ethyl | butyl | ethylene | H | H | 1 | 2 | 0 |
| chloroisopropyl | chloroisopropyl | propylene | H | H | 1 | 2 | 0 |
| bromoethyl | bromomethyl | ethylene | H | H | 1 | 2 | 0 |
| bromopropyl | brompropyl | propylene | H | H | 2 | 1 | 0 |
| ethyl | ethyl | ethylene | methyl | methyl | 1 | 2 | 0 |
| chloroethyl | chloroethyl | propylene | chloromethyl | chloromethyl | 1 | 2 | 0 |
| ethyl | ethyl | chloroisopropylene | H | H | 1 | 1 | 1 |
| tribromoneopentyl | chloroethyl | ethylene | H | H | 1 | 2 | 0 |
| ethyl | ethyl | ethylene | H | H | 1 | 1 | 1 |

The intumescent composition of this invention contains phosphorous acid or phosphoric acid. It is preferred that said composition contain from about 2 to about 25 percent (by weight) of said acid; it is more preferred that said composition contain from about 4 to about 20 percent (by weight) of said acid.

The intumescent composition of this invention also contains water. It is preferred that said composition contain from about 5 to about 50 percent (by weight) of water. In a more preferred embodiment, said composition contains from about 8 to about 40 percent (by weight) of water.

The intumescent composition of this invention may be prepared by means known to the art. One may, e.g., mix in a dry state the methylated trimethylol melamine, phosphorus compound and acid and then add the specified amount of water to the mixture. It is preferred, however, to mix solutions of said compounds together; the concentrations of such solutions are such that, after they are mixed together, the intumescent composition which results contains the specified amounts of water, methylated melamine, acid, and phosphorus compound.

Generally, the components of the intumescent composition of this invention are mixed together for at least about 60 seconds, although longer or shorter mixing times may be used.

The intumescent composition of this invention should be applied to a wood substrate within about 240 minutes of the time it is prepared. Although it is useful for most wood substrates, it is especially useful for imparting durable flame retardancy to a plywood substrate.

Plywood is a material made by bonding wood together with an adhesive. The layers are usually veneer; they are generally no greater than about 0.1875" thick for hardwood plywood and 0.1667" thick for softwood plywood. The successive layers (plies) have their grains at a definite angle to each other, usually 90 degrees.

The intumescent composition of this invention may be advantageously utilized with any of the plywood substrates well known to the art such as, e.g., by spraying, brushing, or coating the composition onto the plywood. It is preferred that the dry solids add on of the intumescent composition of this invention be from about 3 to about 15 grams per square foot of plywood treated. The "add on" is determined by weighing the substrate before and immediately after it is treated. The percent of the solids in the composition applied times this difference is the number of grams of dry solids applied; the number of grams of dry solids applied divided by the number of square feet treated is the "add on" referred to in this specification. One coat of the intumescent composition of this invention may be applied; it is preferred, however, to apply two or more coats.

After the composition of this invention is applied to the wood substrate, it is dried. It may be air dried, in which case up to about 30 hours should be allowed for it to dry. It may be dried by techniques well known to those skilled in the art. If heat is applied to the treated substrate, it is preferred to use a temperature of from about 70 to about 170 degrees centigrade for from about 1 to about 20 minutes. It is more preferred to dry the treated substrate at a temperature of from about 95 to about 110 degrees centigrade for from about 3 to about 10 minutes.

The following examples illustrate the claimed invention and are not to be deemed limitative thereof. Unless otherwise specified, all parts are by weight, all temperatures are in degrees centigrade, all weights are expressed in grams, and all volumes are expressed in milliliters.

EXAMPLE 1

N,N-dimethylol-bis(chloroethyl)phosphoramidate

Thirteen hundred and forty-six grams (4.99 moles) of tris (chloroethyl phosphite) were charged to a three-liter flask equipped with a stirrer and a gas delivery tube. This reactant was cooled with an ice bath to a temperature of less than 20 degrees centigrade; and the addition of chlorine to the tris (chloroethyl phosphite) was commenced. The rate of chlorine addition was maintained so that the temperature of the reaction mixture did not rise above 25 degrees centigrade; chlorine was added to the reaction mixture over a period of 240 minutes until the chlorination reaction was complete (as was indicated by the reaction mixture turning to a yellow color). Dichloroethane by-product was removed from the reaction mixture by reduced pressure distillation. The reaction mixture was then maintained at ambient temperature and allowed to stand overnight.

Ammonia was added to the reaction mixture over a period of about 210 minutes; during the ammonia addition, chloroform was added to maintain the reaction mixture in a fluid state, and the reaction mixture was cooled so that the temperature of the reaction mixture did not exceed about 30 degrees centigrade. The reaction was continued until the ammonia had replaced all of the chlorine which was bonded directly to the phosphorus atom; the reaction was conducted over a period of 210 minutes.

Bis(chloroethyl)phosphoramidate was washed with water and filtered. A white solid with a melting point of 68 degrees centigrade was obtained; it contained 21.69 percent carbon, 4.66 percent hydrogen, 30.6 percent chlorine, 6.05 percent nitrogen, and 13.57 percent phosphorus.

N,N-dimethylol-bis(chloroethyl) phosphoramidate was prepared by dissolving bis(chloroethyl) phosphoramidate in a 37 percent aqueous solution of formaldehyde; about 2.1 moles of formaldehyde per mole of phosphoramidate were present in the reaction mixture. The pH of the reaction mixture was maintained at about 10 during the addition of the formaldehyde to the phosphoramidate; after these reactants formed a solution, however, the pH of the reaction mixture was adjusted to about 7 via the addition of dilute hydrochloric acid to the reaction mixture. The product obtained was dried and subjected to $H^1$ and $P^{31}$ N.M.R. analyses; the spectra obtained were substantially in accordance with those expected from the proposed structure.

EXAMPLE 2

Fifty parts of an 80 percent aqueous solution of Aerotex Resin M-3 ®, a trimethylated trimethylol melamine compound available from the American Cyanamide Corporation, were mixed with 40 parts of diethyl-N,N-bis(2-hydroxyethyl) amino methane phosphonate, 5.0 parts of an 85 percent aqueous solution of phosphoric acid, and 5 parts of water. Two coats of this formulation were brushed onto a lauan plywood sample (which contained a groove and was 24" long, 3.5" wide and 0.1875" thick) to a dry solids add on of 10 grams per square foot. The coated sample was then dried at a temperature of about 100 degrees centigrade for about 5 minutes. Thereafter, the sample was subjected to a two-foot tunnel test to determine its flame spread rate; this test was conducted in substantial accordance with the procedure described in an article entitled "Two-foot Tunnel Test", *Journal of Paint Technology*, Vol. 11, No. 565, February 1972, pp. 43-47; however, the panels were not aged as described in this article.

The two-foot tunnel test is a small scale test designed to simulate the UL Steiner 25-foot tunnel test described by ASTM E84-68. In the former test, the two-foot tunnel was inclined 28 degrees from the horizontal and utilized approximately 96 square inches of test surface. The test specimen was mounted on an angle iron frame in such a way that the surface to be evaluated formed the ceiling of the tunnel. A standard Meeker burner was placed at the lower end of the tunnel, and the specimen was subjected to the flame from this burner for five minutes; during the first four minutes, the length of the advance of the flame front up the inclined panel was recorded at 15 second intervals. The flame lengths were measured by observing the flame front advance through a calibrated window located on the side of the tunnel. The tunnel was calibrated prior to specimen testing by determining the difference in flame lengths of a specimen of asbestos cement board and a specimen of red oak; this difference, by introduction of a constant K, was given a flame spread rating ("FSR") of 100. The flame spread rate calculation was made in accordance with the formula $F.S.R. = (L_n - L_a)K$ wherein F.S.R. was the flame spread rating, $L_n$ was the observed flame of the specimen tested, $L_a$ was the flame for asbestos cement board, $L_o$ was the observed flame length for the red oak sample, and $K = 100/(L_o - L_a)$.

The samples were weighed both before and after being tested in the two-foot tunnel, and the percent weight loss due to combustion of the sample was determined.

The coated plywood sample of this example had a flame spread rating of 25 and lost about 5.5 percent of its weight after the two foot tunnel test.

EXAMPLE 3

A coating formulation containing 50 parts of an 80 percent aqueous solution of trimethylated trimethylol melamine, 40 parts of diethyl-N,N-bis(2-hydroxyethyl) amino methane phosphonate, and 10 parts of an 85 percent aqueous solution of phosphoric acid was prepared. In accordance with the procedure described in Example 2, this formulation was applied to a lauan plywood sample measuring 24.0″×3.5″×0.1875″ to a dry solids add on of 11 grams per square foot and dried; and the coated plywood sample was tested in the two foot tunnel. The coated plywood sample had a flame spread rating of 50 and lost 7 percent of its weight.

EXAMPLE 4

A coating formulation containing 50 parts of an 80 percent aqueous solution of methylated trimethylol melamine, 25 parts of diethyl-N,N-bis(2-hydroxyethyl)amino methane phosphonate, 15 parts of an 85 percent aqueous solution of phosphoric acid, and 10 parts of water was prepared. In accordance with the procedure described in Example 2, this formulation was applied to a lauan plywood sample measuring 24.0″×3.5″×0.1875″ to a dry solids add on of 8 grams per square foot and dried; and the coated plywood sample was tested in the two foot tunnel. The coated plywood sample had a flame spread rating of 20.

EXAMPLE 5

A coating formulation containing 50 parts of an 80 percent aqueous solution of trimethylated trimethylol melamine, 25 parts of a 60 percent aqueous solution of N,N-bismethylol-bis(chloroethyl)phosphoramidate, 15 parts of an 85 percent aqueous solution of phosphoric acid, and 10 parts of water was prepared. In accordance with the procedure described in Example 2, this formulation was applied to a lauan plywood sample measuring 24.0″×3.5″×0.1875″ to a dry solids add on of 9.5 grams per square foot and dried; and the coated plywood sample was tested in the two foot tunnel. The coated plywood sample had a flame spread rating of 50 and lost 9 percent of its weight during the test.

EXAMPLE 6

A coating formulation containing 50 parts of an 80 percent solution of trimethylated trimethylol melamine, 35 parts of diethyl-N,N-bis(2-hydroxyethyl) amino methane phosphonate, 10 parts of an 85 percent aqueous solution of phosphoric acid, and 5 parts of water was prepared. In accordance with the procedure described in Example 2, this formulation was applied to a lauan plywood sample measuring 24.0″×3.5″×0.1875″ to a dry solids add on of 9.0 grams per square foot and dried; and the coated plywood sample was tested in the two foot tunnel. The coated plywood sample had a flame spread rating of 35 and lost 6 percent of its weight during the test.

EXAMPLE 7

A coating formulation containing 50 parts of an 80 percent solution of trimethylated trimethylol melamine, 40 parts of diethyl-N,N-bis(2-hydroxyethyl)amino methane phosphonate, and 10 parts of an 85 percent aqueous solution of phosphoric acid was prepared. Two coats of this formulation were applied to samples of lauan plywood which were 24.0″ long×3.5″ wide×0.1875″ thick to a dry solids add on of 9.0 grams per square foot; one side of each sample was coated, and the coated samples were then dried at a temperature of about 100 degrees centigrade for about 5 minutes.

One of the samples, the "control", was subjected to the two foot tunnel test to determine its flame spread rating and the amount of weight it lost during the test. The other sample was subjected to accelerated aging conditions to determine whether the flame retardant properties of the coating of this invention were affected by heat, water, and ultraviolet light. In accordance with A.S.T.M. test G-26-70, the sample was tested in a "Weather-Ometer" (Model 25/18-WR manufactured by the Atlas Eelectric Device Company of Chicago, Illinois); the sample was maintained at a relative humidity of from about 60 to about 65 percent, and a 120 minute cycle wherein there were 102 minutes of light followed by 18 minutes of light and spray was used. After being subjected to these conditions in the "Weather-Ometer" for 100 hours, the sample was tested in the two foot tunnel to determine its flame spread rating and the amount of weight it lost during the test. The control sample, which was not subjected to accelerated aging, had a flame spread rating of 65 and lost 7 percent of its weight. The sample which had been subjected to 100 hours of exposure had a flame spread rating of 80 and lost about 8 percent of its weight.

EXAMPLE 8

A coating formulation containing 15 parts of an 85 percent aqueous solution of phosphoric acid, 35 parts of diethyl-N,N-bis(2-hydroxyethyl)amino methane phosphonate, and 50 parts of hexamethylanted hexamethylol melamine was prepared. In accordance with the procedure described in Example 2, this formulation was applied to a lauan plywood sample measuring 24.0″×3.5″×0.1875″ to a dry solids add on of 10 grams per square foot and dried for 20 minutes; and the coated plywood sample was tested in the two foot tunnel. The coated plywood sample had a flame spread rating of 50 and lost 7 percent of its weight.

EXAMPLE 9

A coating formulation containing 30 parts of a 30 percent aqueous solution of phosphorous acid, 20 parts of diethyl-N,N-bis(2-hydroxyethyl)amino methane phosphonate, and 50 parts of trimethylated trimethylol melamine was prepared. In accordance with the procedure described in Example 2, two coats of this formulation were applied to a lauan plywood sample measuring 24.0"×3.5"×0.1875" to a dry solids add on of 9.5 grams per square foot and dried; and the coated plywood sample was tested in the two foot tunnel. The coated plywood sample had a flame spread rating of 50 and lost 9 percent of its weight.

COMPARATIVE EXAMPLE 10

A coating formulation containing 50 parts of trimethylated trimethylol melamine and 50 parts of an 85 percent aqueous solution of phosphoric acid was prepared. In accordance with the procedure described in Example 2, this formulation was applied to a lauan plywood sample measuring 24.0"×3.5"×0.1875" to a dry solids add on of 8.0 grams per square foot. A very brittle film which exhibited blistering on its surface was formed.

The above examples have been described for the purpose of illustration, not limitation. Many other modifications will suggest themselves to those skilled in the art; they are intended to be comprehended within the scope of this invention.

The embodiments of this invention in which an exclusive property or privilege is claimed are as follows:

1. An intumescent composition comprising a cyclic nitrogen compound, an acid selected from the group consisting of phosphorous acid, phosphoric acid, and mixtures thereof, water, and an hydroxy-containing organo-phsophorus compound, wherein:

(a) said cyclic nitrogen compound is

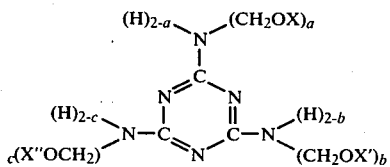

wherein a, b, and c are integers selected from the group consisting of 1 and 2, a plus b plus c equal about 3 to 6, and X, X', and X" are independently selected from the group consisting of hydrogen and —CH₃;

(b) said hydroxy-containing organo-phosphorus compound is selected from the group consisting of

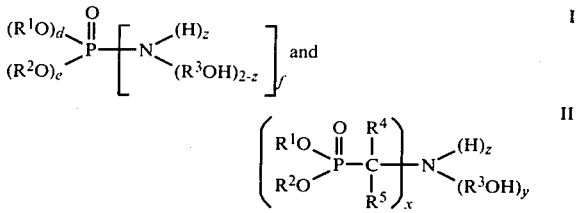

and mixtures thereof, wherein d is an integer of from 0 to 2, e is an integer of from 0 to 2, f is an integer of from 1 to 3, and d plus e plus f equal 3; z is an integer of 0 to 1; x is an integer of 1 to 2, y is an integer of 1 to 2, and x plus y plus z equal 3; $R^1$, $R^2$, and $R^3$ are selected from the group consisting of alkyl radicals containing from about 1 to about 6 carbon atoms and haloalkyl radicals containing from about 2 to about 6 carbon atoms, provided that when $R^3$ is haloalkyl it contains at least 3 carbon atoms; $R^4$ and $R^5$ are selected from the group consisting of hydrogen, alkyl radicals, and haloalkyl radicals, wherein said radicals contain from about 1 to about 6 carbon atoms; and the total number of carbon atoms in the $R^1$, $R^2$, $R^3$, $R^4$, and $R^5$ groups does not exceed about 14.

2. The intumescent composition of claim 1, wherein a plus b plus c equal 3.

3. The intumescent composition of claim 2, wherein at least one of said X, X', and X" groups is —CH₃.

4. The intumescent composition of claim 3, wherein said composition contains from about 30 to about 60 percent of trimethylated trimethylol melamine, from about 10 to about 55 percent of said phosphorus compound, from about 2 to about 25 percent of phosphoric acid, and from about 5 to about 50 percent of water.

5. The intumescent composition of claim 4, wherein $R^1$ and $R^2$ are independently selected from the group consisting of alkyl radicals containing from about 1 to about 4 carbon atoms and haloalkyl radicals containing from about 2 to about 4 carbon atoms; wherein $R^3$ is alkyl of from about 1 to about 4 carbon atoms; and wherein $R^4$ and $R^5$ are hydrogen.

6. The intumescent composition of claim 5, wherein z is 0.

7. The intumescent composition of claim 6, wherein said phosphorus compound is N,N-dimethylol-bis(-chloroethyl)phosphoramidate.

8. The intumescent composition of claim 6, wherein said phosphorus compound is diethyl-N,N-bis(2-hydroxyethyl)amino methane phosphonate.

9. The intumescent composition of claim 8, wherein said composition contains from about 35 to about 50 percent of trimethylated trimethylol melamine.

10. The intumescent composition of claim 9, wherein said composition contains from about 8 to about 40 percent of water.

* * * * *